US00PP33831P2

(12) United States Plant Patent
Hartman

(10) Patent No.: US PP33,831 P2
(45) Date of Patent: Jan. 4, 2022

(54) ***CALADIUM* PLANT NAMED 'CRM STR OF15-691'**

(50) Latin Name: *Caladium X hortulanum*
Varietal Denomination: CRM STR OF15-691

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/193,909

(22) Filed: Mar. 5, 2021

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. Anne Whealy

(57) ABSTRACT

A new and distinct cultivar of *Caladium* plant named 'CRM STR OF15-691', characterized by its short and upright to mounding plant habit; dense and bushy appearance; vigorous growth habit and rapid growth rate; strap/lance-type leaves that are greenish white to lime green in color and variably flushed with dark pink, pale green-colored venation and variably tinged with greyish red, reddish brown or dark red, dark red-colored leaf petiole junction, and thin green-colored margins with dark red-colored edges; and petioles that are almost black in color with pale tannish pink-colored stripes or tannish pink and with brownish black-colored stippling and streaks.

4 Drawing Sheets

Figure 1:
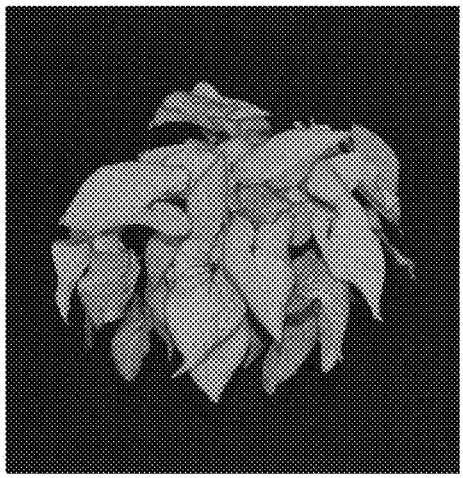

Botanical designation: *Caladium* X *hortulanum*.
Cultivar denomination: 'CRM STR OF15-691'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a strap/lance leaf-type *Caladium* and hereinafter referred to by the name 'CRM STR OF15-691'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2014 in Avon Park, Fla. of *Caladium* X *hortulanum* 'Lemon Blush', disclosed in U.S. Plant Pat. No. 25,450, as the female, or seed, parent with *Caladium* X *hortulanum* 'Flare', disclosed in U.S. Plant Pat. No. 25,426, as the male, or pollen, parent. The new *Caladium* plant was discovered and selected by the Inventor as a single plant within the progeny of the stated cross-pollination in a controlled outdoor nursery environment in Avon Park, Fla. in September, 2015.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2016 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'CRM STR OF15-691'. These characteristics in combination distinguish 'CRM STR OF15-691' as a new and distinct *Caladium* plant:

1. Short and upright to mounding plant habit; dense and bushy appearance.
2. Vigorous growth habit and rapid growth rate.
3. Strap/lance-type leaves that are greenish white to lime green in color and variably flushed with dark pink, pale green-colored venation and variably tinged with greyish red, reddish brown or dark red, dark red-colored leaf petiole junction, and thin green-colored margins with dark red-colored edges.
4. Petioles that are almost black in color with pale tannish pink-colored stripes or tannish pink and with brownish black-colored stippling and streaks.

Plants of the new *Caladium* differ primarily from plants of the female parent, 'Lemon Blush', in the following characteristics:

1. Plants of the new *Caladium* have strap/lance-type leaves whereas plants of 'Lemon Blush' have fancy-type leaves.
2. Leaves of plants of the new *Caladium* are greenish white to lime green in color and variably flushed with dark pink, pale green-colored venation and variably tinged with greyish red, reddish brown or dark red, dark red-colored leaf petiole junction, and thin green-colored margins with dark red-colored edges whereas leaves of 'Lemon Blush' are chartreuse to lime green in color with rose red-colored centers and with development, rose red-colored areas may cover the entire leaf surface.
3. Leaf petioles of plants of the new *Caladium* are almost black in color with pale tannish pink-colored stripes or tannish pink and with brownish black-colored stippling and streaks whereas leaf petioles of plants of 'Lemon Blush' are pink to tannish pink in color with greenish brown-colored stippling and streaks.

Plants of the new *Caladium* differ primarily from plants of the male parent, 'Flare', in the following characteristics:

1. Leaves of plants of the new *Caladium* are greenish white to lime green in color and variably flushed with dark pink, pale green-colored venation and variably tinged with greyish red, reddish brown or dark red, dark red-colored leaf petiole junction, and thin green-colored margins with dark red-colored edges whereas leaves of 'Flare' have rose red-colored centers surrounded by a greyed green and pink-colored speckling and dark green-colored margins.
2. Leaf petioles of plants of the new *Caladium* are almost black in color with pale tannish pink-colored stripes or tannish pink and with brownish black-colored stippling and streaks whereas leaf petioles of plants of 'Flare' are rose red in color.

Plants of the new *Caladium* can be compared to plants of *Caladium* X *hortulanum* 'White Wonder', disclosed in U.S. Plant Pat. No. 21,044. In side-by-side comparisons, plants of the new *Caladium* differ primarily from plants of 'White Wonder' in leaf color as leaves of the new *Caladium* are greenish white to lime green in color and variably flushed with dark pink, pale green-colored venation and variably tinged with greyish red, reddish brown or dark red, dark red-colored leaf petiole junction, and thin green-colored margins with dark red-colored edges whereas leaves of 'White Wonder' are white to grey-green in color with light pink to white-colored venation and dark green-colored borders. In addition, plants of the new *Caladium* differ from plants of 'White Wonder' in leaf petiole color as leaf petioles of plants of the new *Caladium* are almost black in color with pale tannish pink-colored stripes or tannish pink and with brownish black-colored stippling and streaks whereas leaf petioles of plants of 'White Wonder' are tannish green in color with darker-colored stripes.

Plants of the new *Caladium* can also be compared to plants of *Caladium* X *hortulanum* 'White Delight', disclosed in U.S. Plant Pat. No. 21,216. In side-by-side comparisons, plants of the new *Caladium* differ primarily from plants of 'White Delight' in leaf color as leaves of the new *Caladium* are greenish white to lime green in color and variably flushed with dark pink, pale green-colored venation and variably tinged with greyish red, reddish brown or dark red, dark red-colored leaf petiole junction, and thin green-colored margins with dark red-colored edges whereas leaves of 'White Delight' are white to grey-green in color with white-colored main veins and dark green-colored borders. In addition, plants of the new *Caladium* differ from plants of 'White Delight' in leaf petiole color as leaf petioles of plants of the new *Caladium* are almost black in color with pale tannish pink-colored stripes or tannish pink and with brownish black-colored stippling and streaks whereas leaf petioles of plants of 'White Delight' are olive green in color with dark green-colored tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'CRM STR OF15-691' grown in a container that has had its tuber de-eyed prior to planting.

Figure 2:
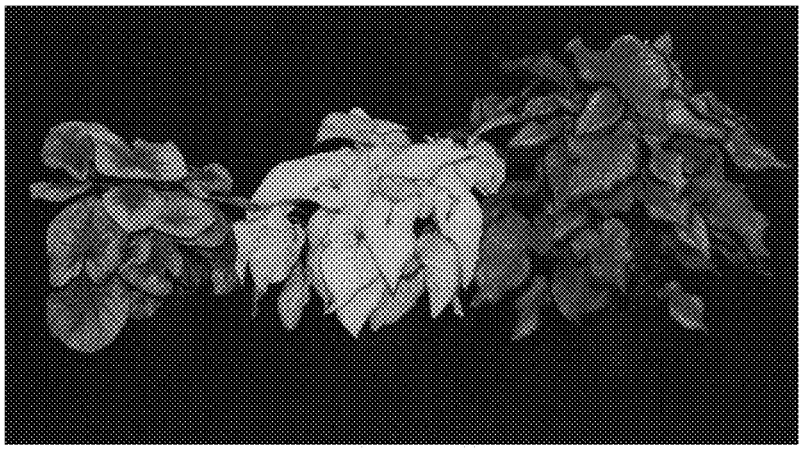

The photograph at the top of the second sheet (FIG. 2) is side perspective view of typical plants of the female parent, 'Lemon Blush' (left), 'CRM STR OF15-691' (center) and the male parent, 'Flare' (right).

Figure 3:
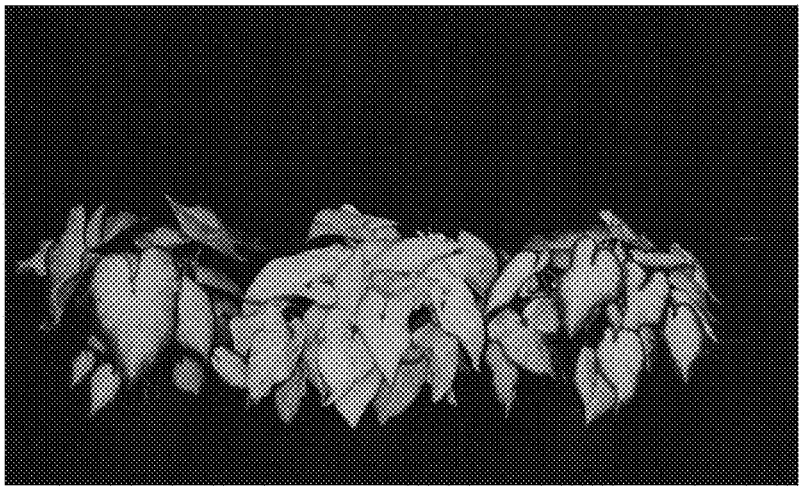

The photograph at the bottom of the second sheet (FIG. 3) is side perspective view of typical plants of 'White Delight' (left), 'CRM STR OF15-691' (center) and 'White Wonder' (right).

Figure 4:
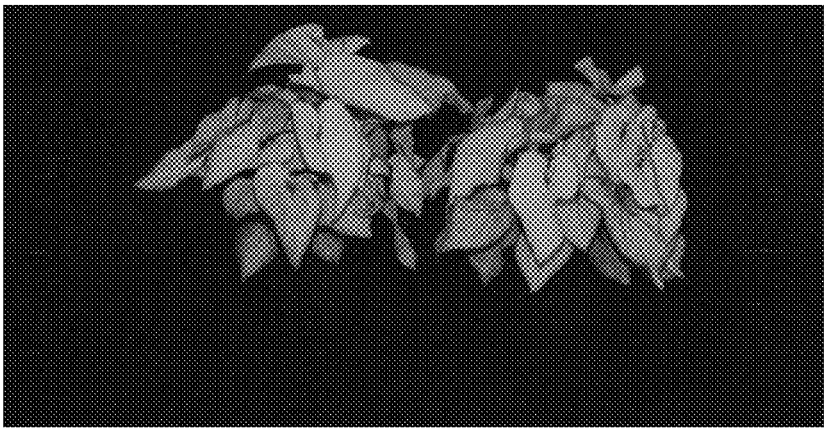

The photograph at the top of the third sheet (FIG. 4) is a comparison view of typical plants of 'CRM STR OF15-691' grown in containers, the plant on the left has not had its tuber de-eyed and the plant on the right has had its tuber de-eyed prior to planting.

Figure 5:
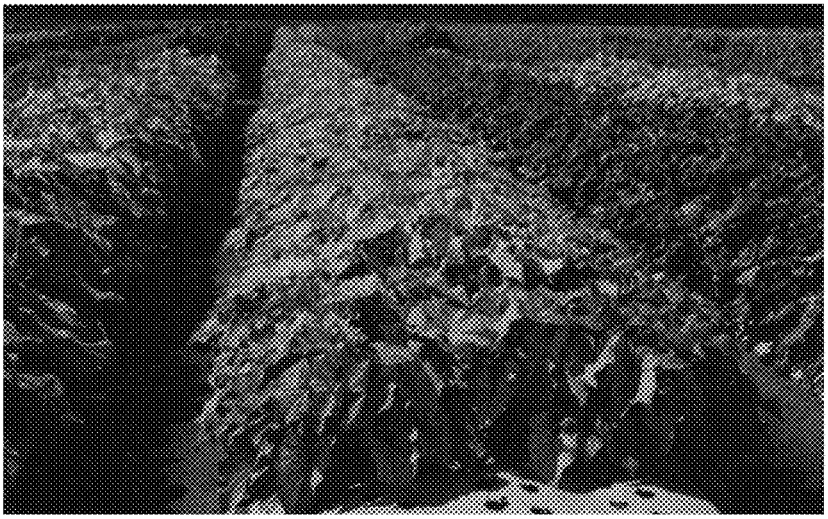

The photograph at the bottom of the third sheet (FIG. 5) is a side perspective view of typical plants of 'CRM STR OF15-691' grown in an open production field.

Figure 6:
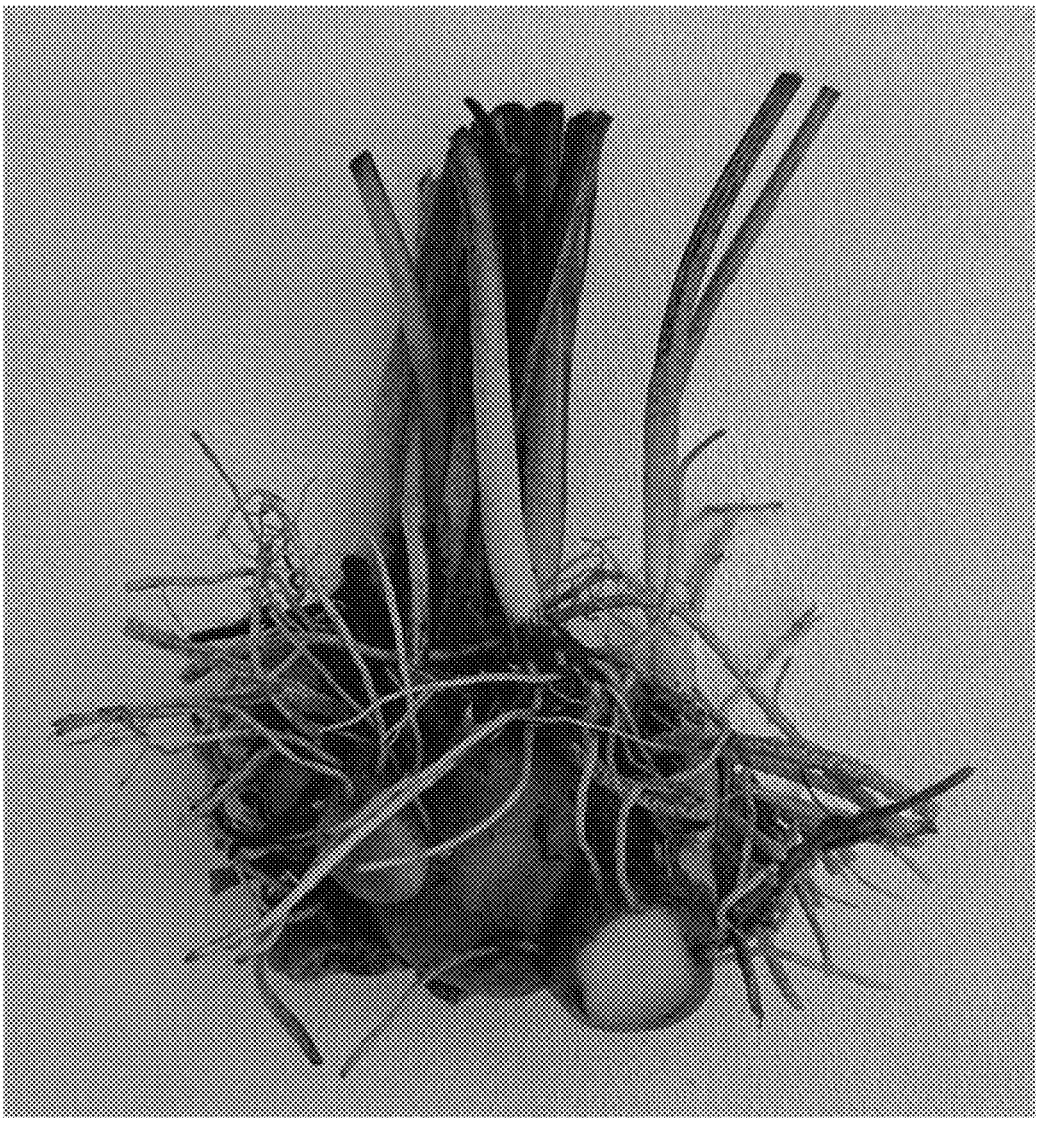

The photograph on the fourth sheet (FIG. 6) is a close-up view of typical freshly-harvested tubers with roots and leaf petioles of 'CRM STR OF15-691'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 750 μmol. During the production of the outdoor nursery-grown plants, day temperatures ranged from about 29° C. to 35° C., night temperatures ranged from about 23° C. to 26° C. and full sunlight conditions. Plants grown in the shade house were eleven weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'CRM STR OF15-691'.

Parentage:

*Female, or seed, parent.*—*Caladium* X *hortulanum* 'Lemon Blush' disclosed in U.S. Plant Pat. No. 25,450.

*Male, or pollen, parent.*—*Caladium* X *hortulanum* 'Flare', disclosed in U.S. Plant Pat. No. 25,426.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments are irregular to ovate in shape. Height: About 4 cm. Diameter: About 4 cm to 6.9 cm. Segment height: About 1.7 cm to 2.2 cm. Segment diameter: About 1.4 cm to 1.6 cm. Axillary bud shape: Roughly triangular. Axillary bud size: About 4.5 mm by 5.5 mm. Texture: Thick, starchy; somewhat brittle. Color: Periderm, freshly-harvested: Close to 199D. Periderm, dried: Close to 200A. Epidermis: Close to 159D. Cortical tissue: Close to 155A to 155D. Axillary buds: Close to 39D. Root description: Thick, fleshy contractile roots with few lateral branches; color, close to NN155C. Rooting habit: Medium density to sparse.

Plant description:

*Plant type.*—Herbaceous perennial; suitable as a potted plant in containers 10-cm to 25-cm and suitable as a landscape plant in shaded areas.

*Plant and growth habit.*—Short and upright to mounding plant habit; dense and bushy appearance; vigorous growth habit and rapid growth rate; potted plants finish in saleable form in about six to eight weeks after planting tubers; leaf petioles and leaves arise from one or more growing points on tubers; leaf petioles initially upright and slightly leaning outwardly with development.

*Plant height, from soil level to top of foliar plane, shade house-grown potted plants.*—When tubers are de-eyed, about 25 cm to 29 cm.

*Plant diameter or spread, shade house-grown potted plants.*—When tubers are de-eyed, about 36 cm to 42 cm.

*Number of shoots per plant, shade house-grown potted plants, tubers de-eyed.*—About six to nine develop per #1 tuber.

*Number of shoots per plant, shade house-grown potted plants, tubers not de-eyed.*—About five to six develop per #1 tuber.

*Cataphylls, shade house-grown potted plants.*—Length: About 3 cm to 4.7 cm. Width: About 1 cm to 1.2 cm. Shape: Lanceolate. Apex: Acute to acuminate. Base: Sheathing the stem. Color, inner and outer surfaces: Close to 200A to 200B.

Leaf description:

*Arrangement and type.*—Alternate; simple; strap/lance-type.

*Length, shade house-grown potted plants, flattened.*—When tubers are de-eyed, about 14.5 cm to 16.5 cm.

*Width, shade house-grown potted plants, flattened.*—When tubers are de-eyed, about 9.5 cm to 10 cm.

*Shape.*—Ovate to lanceolate.

*Apex.*—Acute to acuminate.

*Base.*—Sagittate-peltate; cordate.

*Margin.*—Entire; mostly flat with broad undulations.

*Texture and luster, upper surface.*—Smooth, glabrous; dull sheen.

*Texture and luster, lower surface.*—Smooth, glabrous; slightly glaucous; dull sheen.

*Venation pattern.*—Pinnate and palmate.

*Color, shade house-grown potted plants.*—When developing, upper surface: Interveinal areas: Close to 157D and 193B. Margins: Close to 137D with edges, close to 187B. Basal notch: Close to 187C. Leaf petiole junction: Close to N186A. Midvein: Close to 145B; proximally, variably tinged with close to 178A. Primary veins: Close to 145B to 145C; proximally, variably tinged with close to 178A. Secondary veins: Close to 137D. Peripheral veins: Close to 137C. When developing, lower surface: Interveinal areas: Close to 157D, 145D and 193B to 193C. Margins: Close to 138B with edges, close to 183A. Basal notch: Close to 187C. Leaf petiole junction: Close to 187C. Midvein: Close to 138B. Primary veins: Close to 144B and 144C. Secondary veins: Close to 144C. Peripheral veins: Close to 138A. Fully developed leaves, upper surface: Interveinal areas: Close to 158C, 158D, N155C, 145B, 145C and 182D; towards the margins, close to 184A variably tinged with close to 177A. Margins: Close to 147C and 177A with edges, close to 183A. Basal notch: Close to 187C. Leaf petiole junction: Close to N186C. Midvein: Close to 147D variably tinged with close to 177A and 183A. Primary veins: Close to 177A variably tinged with close to 183A. Secondary veins: Close to 177C or 147D. Peripheral veins: Close to 177A and 177B. Fully developed leaves, lower surface: Interveinal areas: Close to 160D and 159D variably tinged with close to 187B. Margins: Close to 143D with edges, close to 183A. Basal notch: Close to 185A. Leaf petiole junction: Close to 185A. Midvein and primary venation: Close to 146D variably flushed with close to N186C. Secondary veins: Close to lighter than 146D. Peripheral veins: Close to 146D.

*Petioles.*—Aspect: Initially upright and straight and leaning slightly outwardly with development; flexible. Length, shade house-grown potted plants: When tubers are de-eyed, about 16 cm to 27 cm. Diameter, distally, shade house-grown potted plants: When tubers are de-eyed, about 2 mm to 3 mm. Diameter, proximally, shade house-grown potted plants: When tubers are de-eyed, about 4 mm to 5.5 mm. Texture and luster: Smooth, glabrous; distally, glaucous; dull sheen. Color, shade house-grown potted plants: Close to 202A or 200A tinged with close to 147A with streaks and stripes, close to N170D or close to 200A to 200B tinged with close to 147A; or close to N170D with stippling, streaks and stripes, close to 200A to 200B tinged with close to 147A; just below the leaf junction, same as overall colors and flushed with close to 181D. Wing length, shade house-grown potted plants: About 3 cm to 4.5 cm. Wing diameter, shade house-grown potted plants:

When tubers are de-eyed, about 6 mm. Texture and luster, inner and outer surfaces: Smooth, glabrous; dull sheen. Wing color, shade house-grown potted plants: Outer surface: Close to N155C marbled with close to 200A to 200B and tinged with close to 147A; or close to N155C with stippling, streaks and marbling close to 200A to 200B tinged with close to 147A. Inner surface: Close to N155C; colors and patterns on the outer surface are visible on the inner surface.

Inflorescence description: To date, inflorescence development has not been observed on plants of the new *Caladium*.

Pathogen tolerance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'CRM STR OF15-691' as illustrated and described.

* * * * *